United States Patent
Sakiyama-Elbert et al.

(10) Patent No.: US 6,723,344 B2
(45) Date of Patent: Apr. 20, 2004

(54) CONTROLLED RELEASE OF NON HEPARIN-BINDING GROWTH FACTORS FROM HEPARIN-CONTAINING MATRICES

(75) Inventors: Shelly E. Sakiyama-Elbert, Zürich (CH); Jeffrey A. Hubbell, Zurich (CH)

(73) Assignees: Eidgenossische Technische Hochschule, Zurich (CH); Universitat Zurich, Zurich (CH)

( * ) Notice: Subject to any disclaimer, the term of this patent is extended or adjusted under 35 U.S.C. 154(b) by 74 days.

(21) Appl. No.: 09/848,664

(22) Filed: May 3, 2001

(65) Prior Publication Data

US 2002/0146414 A1 Oct. 10, 2002

Related U.S. Application Data

(63) Continuation of application No. 09/298,084, filed on Apr. 22, 1999, now abandoned.

(51) Int. Cl.[7] .............................. A61K 9/14; A01N 1/00; C07K 1/00
(52) U.S. Cl. ................. 424/484; 424/78.1; 424/85.1; 424/279.1; 530/300; 514/2; 514/56
(58) Field of Search ................ 424/484, 78.1, 424/85.1, 279.1; 530/300; 514/2, 56

(56) References Cited

U.S. PATENT DOCUMENTS

| | | | |
|---|---|---|---|
| 4,613,665 A | | 9/1986 | Larm |
| 4,810,784 A | | 3/1989 | Larm |
| 5,100,668 A | | 3/1992 | Edelman et al. |
| 5,693,341 A | | 12/1997 | Schroeder et al. |
| 5,807,982 A | * | 9/1998 | McCaffrey et al. |
| 5,830,700 A | | 11/1998 | Irani |

OTHER PUBLICATIONS

Merck Index (Merck & Co., Inc., Rahway, NJ, 1989) p. 475.*
Hubbell, J.A. et al. Current Opinion in Biotechnology.*
Lyon et al., J. Biol. Chem 272(29)18000–18006, 1997.*
Lee et al., PNAS 88(2768–2772) 1991.*
Schroeder–Tefft, J.A. et al. J. of Controlled Release 48(29–33)1997.*
Kwon G.S. et al., J. of Controlled Release.*
DeBlois, C. et al., Biomaterials 15:9(665–672) 1992.*
Alberts, et al., *Molecular Biology of the Cell*, Garland Publishing, New York, 1994.
Bagheri–Yamand, et al., *J Cancer* 78:111–118 (1998).
Besson, et al., *Analytical Biochemistry* 237:216–223 (1996).
Camarata, et al., *Neurosurgery* 30:313–319 (1992).
Cardin & Weintraub, *Atherosclerosis* 9:21–32 (1989).
Coombs, et al., *J Biol Chem* 237:4323–4328 (1998).
De Raucourt, et al., *J BiomedMater Res* 41:49–57 (1998).
Deblois, et al., *Biomaterials* 15:665–672 (1994).

Dinbergs, et al., *J Biol Chem* 271(47):29822–29829 (1996).
Downs, et al., *Journal Cell Physiological* 152:422–429 (1992).
Edelman, et al., *Biomaterials* 12:619–626 (1991).
Edelman, et al., *Controlled Release Systems Containing Heparin and Growth Factors*, MIT: USA.
Edelman, et al., *Proc Natl Acad Sci USA* 90:1513–1517 (1993).
Edelman, *Journal Clin Invest* 89:465–473 (1992).
Gotz, et al., *Nature* 372:266–269 (1994).
Harada, et al., *Journal Clin Invest* 94:623–630 (1994).
Hata, et al., *J Biol Chem* 268:8847–8457 (1993).
Haugen, et al., *J Neuroscience* 2034–2042 (1992).
Herbert, et al., *Journal Comp Neurological* 365:380–391 (1996).
Higashiyama, et al., *Science* 251(4996):936–9 (1991).
Kallapur, et al., *Journal of Neuroscience Research* 33:538–548 (1992).
Kaneda, et al., *Journal Biochem* 119:1150–1156 (1996).
Kiguchi, et al., *Molecular Carcinogenesis* 22:73–83 (1998).
Kinosaki, et al., *Biochem Biophys Acta* 1384:93–102 (1998).
Lee & Lander, *Proc Natl Acad Sci USA* 88:2768–2772 (1991).
Lin, et al., *Journal Neurochem* 63:758–768 (1994).
Lopez, et al., *Drug Metabolism and Disposition* 24(8):922–924 (1996).
Lopez, et al., *J Pharmacology and Experimental Therapeutics* 282(1):385–390 (1997).
Lyon, et al., *J Biol Chem* 272:1800–1806 (1997).
Maaroufi, et al., *Biomaterials* 18:359–366 (1997).
Maysinger, et al., *Neurosci Lett* 140:71–74 (1992).

(List continued on next page.)

*Primary Examiner*—Yvonne Eyler
*Assistant Examiner*—Michael Brannock
(74) *Attorney, Agent, or Firm*—Holland & Knight LLP

(57) ABSTRACT

Matrices that support cell adhesion and growth are disclosed that deliver low heparin-binding affinity growth factor protein peptides in a controlled manner. These matrices comprise covalently or non-covalently bound heparin or heparin-like polymers, which serve to sequester the low heparin-binding affinity growth factor protein peptides within the matrix. The controlled release of some low heparin-binding affinity growth factor or peptides thereof occurs by degradation of some matrix component or dissociation of the low heparin-binding affinity growth factor protein peptides from the bound heparin. This differs from many controlled delivery devices in that release is not controlled solely by diffusion, and the rate of release may therefore be regulated by altering the rate of degradation of the matrix component or the amount of heparin bound within the matrix. The controlled release of such low heparin-binding affinity growth factor proteins such as NGF-β, NT-3 and BDNF, is demonstrated. The invention also identifies basic domains that can be utilized to identify other low heparin-binding affinity growth factor protein peptides useful in delivery as part of the matrices described herein.

20 Claims, 3 Drawing Sheets

OTHER PUBLICATIONS

McCaffrey, et al., *J Cellular Physiology* 152:430–440 (1992).
Netzel–Arnett, et al., *J Biol Chem* 266:6747–6755 (1991).
Nolo, et al., *European Journal of Neuroscience* 8:1658–1665 (1996).
Powell, et al., *Brain Res* 515:309–311 (1990).
Powell, et al., *Brain Research* 515:309–311 (1990).
Presta, et al., *Biochem Biophys Res Commun* 185:1098–1107 (1992).
Reddi, *Nature Biotechnology* 16:247–252 (1998).
Schense & Hubbell, *Bioconjug Chem* 10:75–81 (1999).
Schroeder, et al., *Affinity Bound Collagen Matrices for the Delivery of Biologically Active Agents*, Collagen Corporation: USA (1997).
Selke, et al., *Am J Physiol* 267:(Heart Circ Physiol. 36):H1303–H1311 (1994).
Shroeder–Teft, et al., *J Controlled Release* 48:29–33 (1997).
Silver, et al., *Biomaterials* 13:339–344 (1992).
Smith, et al., *J Biol Chem* 270:6440–6449 (1995).
Spillmann & Lindahl, *J Biol Chem* 273:15487–15493 (1988).
Steffen, et al., *Growth Factors* 15:199–213 (1998).
Studier, et al., *Expression in E. Coli*, American Press, Inc. 61–89 (1990).
Takagi, et al., *Biochemistry* 14(23):5149–5156 (1975).
Tessler, et la., *J Biol Chem* 269:12456–12461 (1994).
Tyler–Cross, et al., *Protein Science* 3:620–627 (1994).
Zucker & Katz, *Society for Experimental Biology and Medicine* pp. 693–702 (1991).

* cited by examiner

CONTROLLED RELEASE OF NON HEPARIN-BINDING GROWTH FACTORS FROM HEPARIN-CONTAINING MATRICES

This is a continuation of U.S. Ser. No. 09/298,084 filed Apr. 22, 1999, now abandoned.

FIELD OF THE INVENTION

The present invention relates to the field of three-dimensional matrices that contain pharmacologically active molecules, particularly growth factors. The invention also relates to the use of growth factors or proteins in a matrix designed to promote cell and tissue growth. The invention further relates to the use of growth factors with low heparin-binding affinity. In addition, the invention relates to the field of articles of manufacture useful as implantable devices and wound dressings as the matrix of the invention is designed to be used in conjunction with such devices to provide protracted and controlled release of growth factor, thus promoting wound healing in the patient.

BACKGROUND

Many growth factors are thought of as "heparin-binding" growth factors. Families with one or more members that bind heparin include fibroblast growth factors and bone morphogenetic proteins (BMPs) (1, 2). Additional growth factors that bind heparin include transforming growth factor β1 (TGF-β1), interleukin-8, neurotrophin-6, vascular endothelial cell growth factor, heparin-binding epidermal growth factor, hepatocyte growth factor, connective tissue growth factor, midkine, and heparin-binding growth associate molecule (3–11). These factors have shown the potential to enhance healing in many different types of tissue including vasculature, skin, nerve, and liver.

Controlled delivery devices based on heparin-affinity of these growth factors have been designed previously (12–14). These drug delivery devices have previously been used to deliver "heparin-binding" growth factors. Such "heparin-binding" growth factors are typically considered to be those which bind to heparin with a relatively high affinity, often characterized by elution from heparin-affinity columns at NaCl concentrations well above physiological levels (>140 mM). In such delivery systems, the heparin-binding affinity of the growth factor is usually used to sequester the growth factors to immobilized heparin of some form. For example, Edelman et al. have used heparin-conjugated Sepharose beads to bind basic fibroblast growth factor (bFGF) and then encapsulated the beads with alginate (12, 19). These beads serve as reservoirs that release bFGF slowly based on the binding and dissociation constants of bFGF and heparin.

The delivery of "non-heparin-binding growth factors" has previously required release methods for delivery typically based on diffusion-controlled release of the factors from porous materials (15–18). There remains a need in the medical arts for a device that is capable of providing the release of low heparin-binding growth factors at a controlled and predictable rate in order-to provide effective release of the factor over a clinically useful period during the wound healing process.

SUMMARY OF THE INVENTION

In a general and overall sense, the present invention relates to the use of how non-heparin-binding growth factors in delivery techniques employing growth factors with heparin-affinity by utilizing low heparin affinity sequences present in many proteins. The particular growth factors employed as part of the invention have been found by the present inventors to possess a basic sequence at a site in the protein that is freely accessible in the proteins native conformation. This basic region may possess only relatively low heparin-affinity.

As used in the description of the present invention, "low-heparin-binding affinity" of a growth factor or peptide fragment thereof is defined as any protein, peptide, or derivative or combination thereof, that is capable of demonstrating the biological activity of a growth factor, and that has a relatively binding low affinity for binding heparin, and will elute from a heparin-affinity column at sub-physiological NaCl concentrations. Physiological levels of NaCl may be defined as about 140 mM NaCl. Herein the term "sub-physiological" levels of NaCl, therefore, may be further defined as from between about 25 mM to about 140 mM NaCl. Although low heparin-binding affinity growth factors elute from heparin-affinity columns at sub physiological NcCl concentrations, their low affinity for heparin can still be used to sequester the protein or peptide to a matrix that contains heparin or a heparin-binding site.

By way of example, and in no way intending to be limited to any particular mechanism of action, the invention may be described as employing a matrix having growth factor proteins with a relatively high-ratio of heparin-binding sites. A ratio of at least 1:1 heparin to growth factor must be used, but the greater the excess of heparin sites the slower the release. In this fashion, primarily "non-heparin-binding" growth factors or peptide fragments thereof with relatively low heparin-binding affinity can be bound to a heparin-decorated matrix. These matrices can then serve as reservoirs containing the growth factor or factors to be delivered. The dissociation kinetics of low affinity heparin-binding proteins are relatively fast, but the high number of binding sites allows rebinding of the growth factor before it can diffuse out of the matrix. Release can occur by diffusion of the growth factor out of the matrix prior to rebinding, or it can occur if the growth factor encounters a cell surface receptor before rebinding to a heparin site. In this fashion, release of the growth factor or bioactive fragment thereof can be sustained, and continue to foster improved healing.

In a general and overall sense, the present invention describes in at least one aspect a specially designed matrix that provides for the release of growth factors or bioactive fragments thereof. The growth factor is defined as having low binding affinity for heparin. The matrix, more particularly, may be defined as comprising a substrate capable of providing attachment of heparin, a heparin-like polysaccharide, or a heparin-like polymer, and a growth factor or peptide fragment thereof having a basic domain that binds heparin with low affinity.

The characteristic of the growth factor or peptide fragment thereof as binding to heparin with low affinity may be further described as a peptide/protein that will elute from a heparin affinity column at an NaCl concentration of about 25 mM to about 140 mM.

The "low heparin-binding affinity" growth factor or peptide fragment thereof may be further defined as comprising a length of about 8 to 30 amino acid residues. This sequence of amino acid residues, in some embodiments, may be defined as comprising at least 2 basic amino acid residues, a ratio of basic to acidic amino acid residues of at least 2, and a ratio of hydrophobic amino acid residues to basic amino acid residue of at least 0.67. The growth factor or fragment thereof elutes from a heparin affinity column at less than 140 mM or at about 25 to aboutl 40 mM NaCl.

For purposes of this application, basic amino acids may be defined as K (lysine) or R (arginine). The acidic amino acid residues may be further defined as D (aspartic acid) or E (glutamic acid). The hydrophobic amino acid residues may be defined as A (alanine), V (valine), F (phenylalanine), P (proline), M (methionine), I (isoleucine), or L (leucine). For purposes of this application, C (cysteine) that are involved in a disulfide bridge are also considered hydrophobic.

By way of example, the low heparin-binding affinity growth factor or a peptide fragment thereof as defined in the invention comprises neurturin, persephin, IGF-1A, IGF-1β, EGF, NGFβ, NT-3, BDNF, NT-4, TGF-β2, TGF-β3, TGF-β4, or a peptide fragment of any one of these. Other growth factors may be found which contain similar basic domains that are not enumerated here. The matrix itself may also comprise any of a variety of materials, such as fibrin, collagen, hyaluronic acid, or a synthetic polymer hydrogel. By way of example, the synthetic polymer hydrogel may be a poly (ethylene glycol) hydrogel or a derivative thereof. Other synthetic polymer hydrogels may be used apart from those enumerated here.

The peptides of the invention that bind heparin with high affinity have a characteristic amino acid domain that will not elute from a heparin-affinity column at less than 140 mM NaCl. While many potential peptides exist, the inventors have identified several peptide sequences in particular. These are exemplified in the amino acid sequences identified in SEQ. ID. NO.:1, SEQ ID. NO.:2; SEQ ID. NO.:3; SEQ ID. NO.:4; and SEQ ID. NO.:5. Many other peptides may be used apart from the specifically enumerated sequences here.

The heparin or heparin-like polysaccharides of the invention may be further characterized, at least in some embodiments, as having a molecular weight of at least 3,000 Daltons. It is contemplated that virtually any molecular weight heparin or heparin-like polysaccharide could be used in the practice of the invention of at least 3,000 Daltons, without any upper molecular weight limitation. For practical purposes a molecular weight maximum of 10,000,000 may be considered. In particular applications, the heparin-like polysaccharide may be further defined as a polysaccharide having a molecular weight of at least 3,000 Daltons and having at least one negative charge per two saccharide rings and no more than one positive charge per ten saccharide rings.

Examples of heparin-like polysaccharide include dextran sulfate, chondroitin sulfate, heparin sulfate, fucan, alginate or derivatives thereof. The present inventors have found that particular preparations of the matrix that include a particular molar ratio of heparin to growth factor, such as a molar ratio of 1, may be employed in the practice of the invention. It has further been found that a matrix of the invention that includes a molar ratio of covalently-attached peptide having a binding domain that binds heparin with high affinity to heparin or a heparin-like polysaccharide of at least one is in some embodiments of the matrix a preferred ratio. These heparin and heparin-like polysaccharides may be either covalently attached to the substrate or immobilized via non-covalent interactions (i.e. electrostatically bound). Synthetic polymers may be designed that function in a heparin-like manner.

The substrate of the matrix as defined in the present invention may comprise fibrin, collagen, hyaluronic acid, a synthetic polymer gel, a mixture thereof, or any variety of synthetic derivatives thereof, that is capable of supporting the attachment of the types of peptides described there, and/or cells.

The matrix and various embodiments of the matrix described herein provide a multitude of advantages, particularly when employed at tissue sites where a wound healing response is desired. The growth factor or peptide fragment thereof provided in the matrix is released by the degradation of a component of the matrix, by the disassociation of growth factor from the heparin or heparin-like polysaccharide, or by a combination of these mechanisms. In this manner, a more sustained and controlled, release of growth factor into the site where the matrix is implanted may be achieved. Methods for providing the controlled release of growth factor at a wound site in need thereof are provided by the present invention. The growth factor for such applications may include TGF-β3, which may be particularly useful in dermal healing. The invention provides various articles of manufacture, such as a vascular graft or shunt, or tissue replacement that includes the matrix defined in this disclosure. Such articles may in some embodiments be defined as implantable sterilized compositions. The heparin-binding peptide used in the present examples possesses high heparin affinity.

In addition to using protein matrices as the substrate of the delivery system, other types of matrices can be used. Synthetic polymer hydrogels, including hydrogels formed by photopolymerization or conjugate addition reactions, can be utilized as the substrate for the delivery device. This synthetic material may contain cell adhesion domains, substrates for enzymatic degradation or hydrolysis, heparin-binding domains, or covalently bound heparin. Through either the covalent or non-covalent attachment of heparin, such synthetic matrices can bind low heparin-binding affinity growth factor proteins and release them in a controlled manner. Release can occur by degradation of matrix components or dissociation of the low heparin-binding affinity growth factor proteins, just as in protein matrices.

The substrate for the delivery system can also include matrices of hyaluronic acid or hyaluronic acid derivatives. Such materials are commonly used and readily available. The addition of covalently or non-covalently bound heparin or heparin-like polysaccharides can be used to provide controlled delivery of low heparin-binding affinity growth factor proteins. Release can occur by degradation of matrix components or dissociation of the low heparin-binding affinity growth factor proteins, just as in protein or synthetic polymer matrices.

In addition to heparin, other heparin-like polymers have similar binding affinity for heparin-binding proteins and peptides. Such heparin-like polymers include, for example, dextran sulfate, chondroitin sulfate, heparin sulfate, fucan and alginate (See Maaroufi, et al, 1997 (46) and Logeart, et al., (1997) (47). In addition, synthetic heparin-like polymers or polysaccharide derivatives also exist, which have similar binding affinity for heparin-binding proteins or peptides as heparin. Examples of heparin-like polysaccharide derivatives include dextran derivatives such as those made by de Raucourt, et al., (1998) (48) and Bagheri-Yamand, et al., (1998) (49). Examples of heparin-like synthetic polymers include those by Silver, et al., (1992) (50). For the purposes of this invention, usage of the term "heparin" is considered to include all heparin-like polymers and polysaccharides including those described above.

(1) Amino acid three-letter and one-letter abbreviations:

| Abbreviation 3 letter | Abbreviation 1 letter | Amino Acid Name |
|---|---|---|
| Ala | A | Alanine |
| Arg | R | Arginine |
| Asn | N | Asparagine |
| Asp | D | Aspartic Acid |
| Cys | C | Cysteine |
| Glu | E | Glutamic Acid |
| Gln | Q | Glutamine |
| Gly | G | Glycine |
| His | H | Histidine |
| Ile | I | Isoleucine |
| Leu | L | Leucine |
| Lys | K | Lysine |
| Met | M | Methionine |
| Phe | F | Phenylalanine |
| Pro | P | Proline |
| Ser | S | Serine |
| Thr | T | Threonine |
| Trp | W | Tryptophan |
| Tyr | Y | Tyrosine |
| Val | V | Valine |

The following sequences are referenced in the description of the present invention.

| | | |
|---|---|---|
| SEQ ID NO: 1 | ATIII domain | K(βA)FAKLAARLYRKA |
| SEQ ID NO: 2 | PF4 domain | YKKIIKKL |
| SEQ ID NO: 3 | NCAM domain | KHKGRDVILKKDVR |
| SEQ ID NO: 4 | ATIII domain modified | R(βA)FARLAARLYRRA |
| SEQ ID NO: 5 | bFGF domain | KDPKRLYRSRKY |
| SEQ ID NO: 6 | NGF basic domain | CVLSRKAVRRA |
| SEQ ID NO: 7 | NT-3 basic domain | CALSRKIGRT |
| SEQ ID NO: 8 | BDNF basic domain | CTLTIKRGR |

Figure 1:
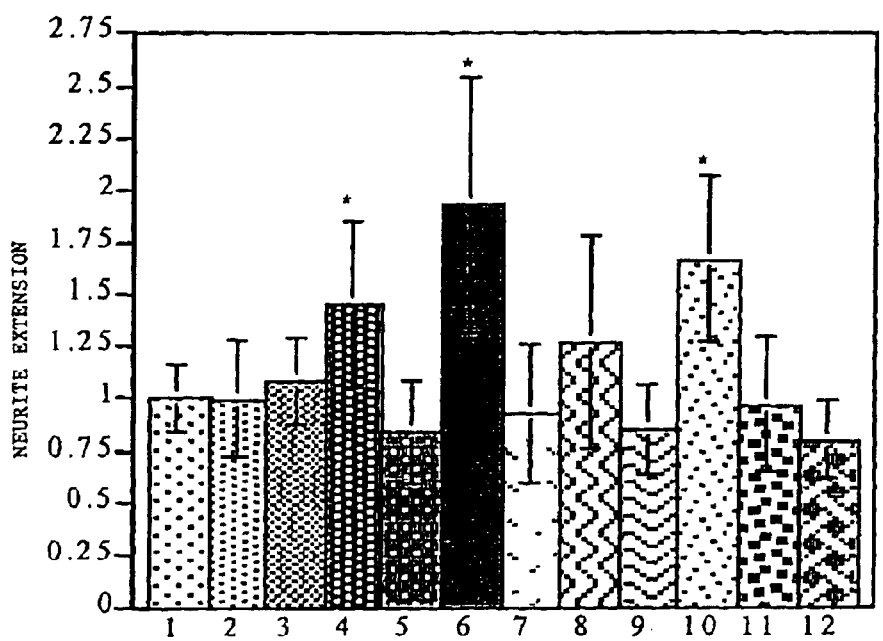
FIG. 1

Effect of matrix bound basic fibroblast growth factor on neurite extension from dorsal root ganglia in three-dimensional fibrin gels. Ganglia were dissected from day 8 chick embryos and placed in prewashed fibrin gels. * denotes p<0.05 versus unmodified fibrin. The soluble treatments contain bFGF, but not heparin or heparin-binding peptide. These treatments show no difference from unmodified fibrin suggesting that the washing protocol used was sufficient to remove unbound growth factor. The results also suggest that peptide, heparin, and growth factor is all necessary components of the controlled release system.

Bar 1, fibrin; Bar 2, with Peptide+heparin; Bar 3, 0.1, μg/ml bound; Bar 4, 1.0 μg/ml bound; Bar 5, 1.0 μg/ml soluble; Bar 6, 5.0 μg/ml bound; Bar 7, 5.0 μg/ml bound; Bar 8, 1.0 μg/ml culture; Bar 9, VEGF 1.0 μg/ml; Bar 10, 1.0 μg/ml bound to 50% peptide; Bar 11, 1 μg/ml+soluble ATIII; Bar 12, 1 μg/ml+heparin (no peptide). "Bound" refers to fibrin, with Peptide and heparin. "Soluble" refers to fibrin.

FIG. 2

Effect of matrix bound NGF-β, NT-3 and BDNF on neurite extension from dorsal root ganglia in three-dimensional fibrin gels. Ganglia were dissected from day 8 chick embryos and placed in prewashed fibrin gels. * denotes p<0.05 versus unmodified fibrin. The soluble treatments contain growth factor, but not heparin or heparin-binding peptide. These treatments show no difference from unmodified fibrin suggesting that the washing protocol used was sufficient to remove unbound growth factor.

Bar 1, fibrin; Bar 2, NGF bound at 0.1 μg/ml; Bar 3, NGF soluble at 0.1 μg/ml; Bar 4 BDNF bound at 0.1 μg/ml; Bar 5, BDNF soluble at 0.1, μg/ml bound; Bar 6, NT-3 bound at 1.0 μg/ml; Bar 7, NT-3 soluble at 0.1 μg/ml bound. "Bound" refers to fibrin, with Peptide and heparin. "Soluble" refers to fibrin.

FIG. 3

Ability of matrix bound NGF-β to promote neurite extension from dorsal root ganglia in three-dimensional fibrin gels as a function of wash time prior to cell seeding. Ganglia were dissected from day 8 chick embryos and placed in prewashed fibrin gels. * denotes p<0.05 versus unmodified fibrin. The soluble treatments contain growth factor, but not heparin or heparin-binding peptide. This assay demonstrates that the matrix bound NGF-P maintains its activity for 4 days while the unbound NGF-β is not active after 1 day of washing.

——■—— fibrin;  ——♦—— ngf bound (100 ng/ml);  ——●—— ngf soluble (100 ng/ml)

DETAILED DESCRIPTION OF THE PREFERRED EMBODIMENTS

The present invention provides compositions useful in promoting the controlled release of low affinity-heparin-binding growth factors having a low heparin-binding domain of about 8 to about 30 basic amino acids in length.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Heparin-Affinity Chromatography of Hepanir-Binding and Low Affinity Heparin-Binding Growth Factors Heparin-affinity chromatography is a method commonly used to determine the relative affinity of heparin-binding proteins. If a protein elutes at NaCl concentrations near or below physiological level (approximately 140 mM) it is not to be considered "heparin-binding" for purposes of the description of the present invention. This is because the growth factors would dissociate rapidly from heparin in vivo.

The relative affinity for heparin of proteins was determined by heparin-affinity chromatography, using a TSK- GEL Heparin-5PW (7.5 cm×7.5 mm ID) column (TosoHass, Stuttgart, Germany). Samples of the protein were injected in 20 mM Tris, pH 7.4, 0.05 M NaCl. Elution was accomplished by running a gradient of NaCl from 0.05 M to 2.0 M over 30 min, and the NaCl concentration at which elution was observed was taken as a measure of the heparin-binding affinity of the protein. The relative heparin-binding affinity of proteins not previously reported in the literature to be heparin-binding was determined and compared with proteins such as bFGF and antithrombin III, which are know to be strongly heparin-binding. The results are shown in Table 1.

The two "non-heparin-binding" growth factors, TGF-β2 and NGFβ both eluted at sub-physiological NaCl concentrations, suggesting that they have relatively low heparin-binding affinity, and will rapidly dissociate from heparin under physiological conditions. The two heparin-binding proteins, antithrombin III and bFGF, elute at NaCl concentrations that are much greater than physiological levels.

Others have also used heparin to increase the activity of and prevent the degradation of growth factors. Schroeder et al. (20) used heparin to increase the stability of TGF-β1 and prevent loss of activity. They have also attached heparin to collagen and employed the heparin-TGF-β1 complex in collagen gels to show that such heparin-based systems can improve growth factor activity in vivo by controlled release (21). TGF-β1 is known to possess strong heparin binding affinity. However, such heparin-based release systems have not been tested previously with growth factors, which are considered to have low heparin-binding affinity (those which are characterized by elution from heparin-affinity columns at sub-physiological NaCl concentrations).

Analysis of the primary sequence of proteins by the present inventors, including growth factors, has revealed that the primary sequence may contain regions that are basic in nature and as that the basic residues are commonly flanked by hydrophobic residues. These sequences are generally of a similar nature to the XBBXBX heparin-binding consensus (where X is a hydropathic residue and B is a basic residue) the heparin-binding consensus was described by Cardin and Weintraub (22). However, the exact sequence of the basic regions vary from protein to protein. The three-dimensional structure for many proteins is also available, which allows the location of basic regions to be determined. In order for basic regions to be useful for sequestration of a protein, they must be located on the surface of the protein. Frequently, such regions are observed to occur in the amino or carboxy terminus of the protein.

TABLE 1

NaCl concentration required to elute proteins from a heparin-affinity column.

| Protein | [NaCl] require to elute peptide |
|---|---|
| bFGF | 2.0 M |
| antithrombin III | 1.58 M |
| TGF-β2 | 0.05 M |
| NGFβ | 0.05 M |

EXAMPLE 2

In Vitro Model for Bioactivity—Neurite Extension

The present example is provided to describe the model for assaying in vitro bioactivity of materials described herein.

A three-dimensional fibrin gel in vitro model for assay neurite extension. Fibrinogen was dissolved in water and dialyzed into Tris-buffered saline (TBS) at pH 7.4 for 24 hr. The concentration of fibrinogen was determined by measuring the absorbance at 280 nm. Fibrin gels were made containing a final concentration of 3.5 mg/ml fibrinogen, 2.5 mM $Ca^{++}$, and 2 NIH units/ml thrombin in TBS. The polymerization mixture was incubated for 60 min at 37° C., 95% relative humidity, and 5% $CO_2$.

After polymerization, 1 ml TBS was added to each well. The gels were washed 5 times over 24 hr, with the first 4 wash solutions consisting of TBS and the last solution consisting of modified neural basal medium. Dorsal root ganglia (DRGs) were dissected from day 8 chick embryos and placed in Hanks-buffered salt solution. The ganglia were placed inside the fibrin gels (one per well) and the gels were incubated for 60 min at 37° C., 95% relative humidity, and 5% $CO_2$. After 60 min, 1 ml of modified neural basal medium was added to each well. The media was changed at 24 hr. Bright field images of the ganglia were taken at 24 and 48 hr. The images were analyzed to determine the average length of neurite extension, which was calculated to be the area of an annulus between the DRG body and the outer halo of extending neurites, as shown by Herbert et al. (1996) (23). Neurite extension for each experiment was normalized by the average neurite extension through unmodified fibrin gels from the same experiment and time point. Results are shown in FIG. 1, Bar 1. This study demonstrates the utility of the invention as a cell support and growth material that will enhance neurite extension in three-dimensions. This is also demonstrated of the utility the invention would have for promoting cell growth and neurite extension under conditions found in vivo.

EXAMPLE 3

Release of Bioactive Neurotrophins from Heparin-Based Delivery Stystem

An Example of a growth factor that is not considered to be heparin-binding growth factors, but that contains a basic sequence is nerve growth factor β (NGFβ) growth factor. This growth factor is considered to be non-heparin-binding and has even been used as a negative control for a heparin-binding protein in heparin-binding analysis (See Lee and Lander (1991) (24). However, NGF contains a basic domain at its C-terminus amino acid position (230–241 of human NGF beta) consisting of the following residues: CVLSRKAVRRA (SEQ ID NO:6). Similar basic domains can be found in the carboxy termini of neurotrophin-3 (NT-3, CALSRKIGRT, 248–257 of human NT-3, SEQ ID NO: 7) and brain-derived neurotrophic factor (CTLTIKRGR, 238–247 of human BDNF, SEQ ID NO: 8).

The present example demonstrates that NGFβ, NT-3 and BDNF can be delivered in a sustained manner from heparin-containing fibrin matrices that contain non-covalently immobilized heparin. This system consists of covalently immobilized heparin-binding peptides cross-linked to the fibrin matrix by factor XIIIa (See Schense and Hubbell (1999) (25) and heparin, which is non-covalently attached to these heparin-binding peptides. These materials have been shown by the present inventor to effectively deliver heparin-binding growth factors, such as basic fibroblast growth factor. (U.S. Ser. No. 09/141770, specifically incorporated herein by reference). With this system, a bi-domain peptide is synthesized to comprise a heparin-binding sequence in one domain and a substrate for the coagulation enzyme factor XIIIa in the other domain (Schense and Hubbell, (1999) (25)). This enzyme covalently attaches the substrate domain of the bi-domain peptide to the fibrin network during coagulation, thereby also immobilizing the heparin-binding domain of the bi-domain peptide to the fibrin network. Heparin is also included into the coagulation mixture, and the heparin is thereby immobilized to the fibrin network by binding to the immobilized peptide.

The release system was first characterized with growth factors that demonstrate strong heparin binding affinity. The results of these studies are shown in FIG. 1. Bar 1 shows the neurite extension through unmodified fibrin gels. Bar 2 shows that the release system, consisting of heparin and incorporated heparin-binding peptide, does not promote neurite extension without the addition of growth factor. Bars 3, 4 and 6 show the dose-response effect of matrix-bound bFGF, which enhances neurite extension by up to 100% (bar 6). Bars 5 and 7 show that when bFGF is added during polymerization of the fibrin gel in the absence of the release system, it does not enhance neurite extension, presumably because it diffuses out of the fibrin too quickly. Bar 8 shows that the presence of bFGF in the culture media promotes neurite extension similar to that of matrix bound bFGF at the same concentration. Bar 9 shows that VEGF does not enhance neurite extension, demonstrating that the growth factor bound must also show bioactivity in neural models to promote neurite extension. Bar 10 shows that when the amount of heparin-binding sites is decreased by 50%, the release of growth factor is not significantly affected. This deviation supports the contention that a high excess of growth factor binding sites is present. Bar 11 shows that when the peptide is cross-linked to the matrix, it will constitute a functional heparin-based delivery system. Bar 12 demonstrates that heparin and bFGF without the immobilized heparin-binding peptide do not constitute a functional delivery system and that heparin and immobilized peptide will enhance and sustain the sustained release of growth factor. These results demonstrate that the delivery system is capable of sustained release of a heparin binding growth factor in an active form.

Figure 2:
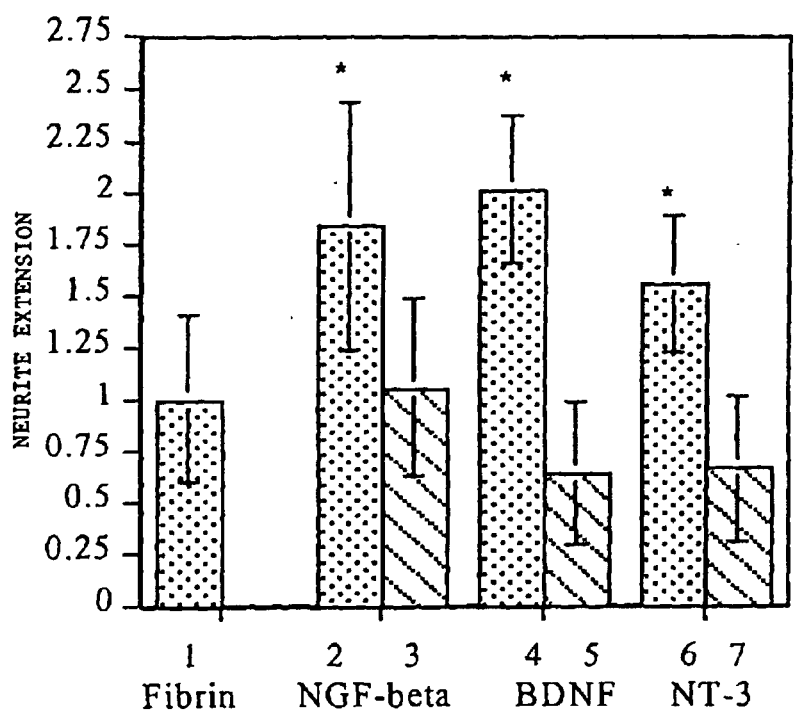

The ability of heparin-containing fibrin matrices to deliver low-heparin-binding growth factors has been tested using NGF-β, NT-3 and BDNF, all members of the neurotrophin family. Fibrin gels were made as described in Example 2, except for the addition of peptide, heparin and neurotrophin described below. Fibrin gels were made containing a final concentration of 3.5 mg/ml fibrinogen, 2.5 mM Ca++, 2 NIH units/ml thrombin, 0.25 mM peptide, 0.125 mM heparin, and 0.1 μg/ml of the neurotrophin to be tested. Otherwise, the assay was performed as described in Example 2. The results are shown in FIG. 2. The fibrin group represents the behavior of normal fibrin and was the control data set to which neurite extension was normalized. These ganglia were cultured in the presence of 20 ng/ml NGF. All other treatments contained no growth factors in the media. For each of the three neurotrophins tested, neurite extension was enhanced only when the heparin-based delivery system of peptide and heparin was present and bound to the matrix ("bound" bars). The addition of neurotrophin alone ("soluble" bars) without peptide or heparin did not enhance neurite extension presumably because the factor diffused out of the fibrin too quickly. The materials shown in FIG. 2 differ from those in FIG. 1 in that "low-heparin-binding affinity" growth factors were released in FIG. 2, while the factors released in FIG. 1 are considered strongly heparin-binding. This distinction is clearly demonstrated in Example 1, in which the heparin-binding growth factor (bFGF) eluted from heparin above physiological NaCl concentrations, whereas the low and non-heparin-binding growth factors (NGF-β, and TGF-β2) eluted at sub-physiological NaCl concentrations. In both cases, the heparin-based delivery systems were able to deliver bioactive growth factors in a controlled manner. This demonstrates, surprisingly, that non-heparin-binding growth factors can be released in a sustained manner from heparin-containing matrices.

Figure 3:
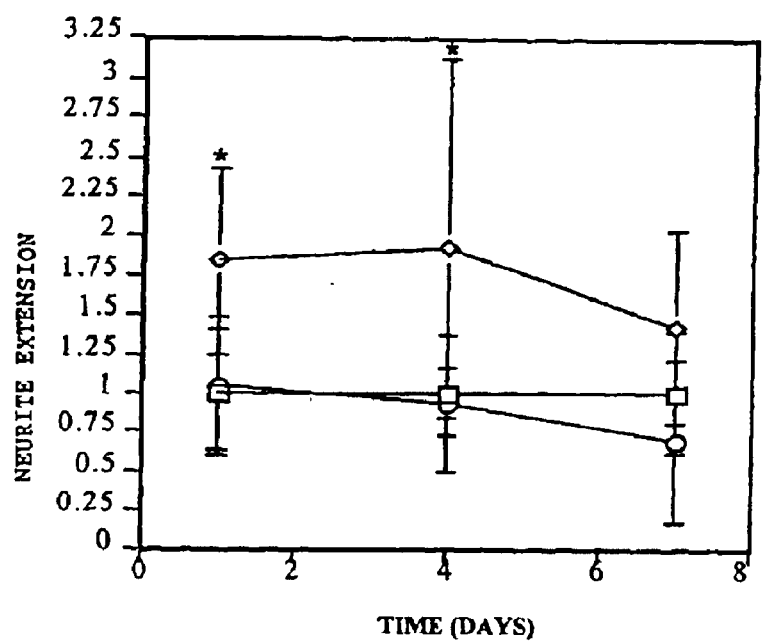

To determine how long the release of low-affinity growth factors could be sustained, NGF-β-containing gels were washed for extended time periods prior to cell seeding. In each case, the gels were washed thoroughly with TBS. The results are shown in FIG. 3. The bioactivity of the growth factor present after 4 days is the same as after 1 day of washing. After 1 week of washing, the bioactivity of the growth factor released is decreased.

These results demonstrate that NGF-β, NT-3 and BDNF are being sequestered by heparin and that the increase in outgrowth versus unmodified fibrin is due to matrix bound growth factor, rather than free growth factor. This demonstrates that such heparin-based materials can be used to sequester proteins with low heparin-binding affinity, which contain exposed basic regions. In this three-dimensional fibrin matrix, heparin was immobilized at approximately 380 μg/ml. This material demonstrated NGF release over approximately one week. There are situations when release for as little as a day would be therapeutically useful. Thus a useful amount of immobilized heparin would be at least 95 μg/ml, with higher amounts leading to release sustained over longer periods.

The results shown here demonstrate that "non-heparin-binding growth factors", such as NGFβ, BDNF and NT-3, can be released in a controlled manner from heparin-based drug delivery systems based on their low affinity for heparin. These proteins can be sequestered within three-dimensional materials containing immobilized heparin based on basic domains found in the proteins. Furthermore, the growth factors released from these systems retain bioactivity in in vitro models as shown above. This demonstrates other low heparin-binding affinity growth factor proteins containing similar types of basic domains could be released from heparin-based delivery systems in a similar manner.

EXAMPLE 4

Members of the TGF-β Family

The approach to sequence analysis described above can be applied to growth factors from other families as well. A list of growth factors and their sequences is shown in Table 2, which shows domains that may have low heparin-binding affinity and could be released from heparin-based delivery systems such as those described above. These factors include some members of the TGF-β family, namely TGF-β2, TGF-β3, and TGF-β4. TGF-β2, TGF-β3 and TGF-β4 are members of a family, which contains one strongly heparin-binding growth factor, TGF-β1. However, other members of the TGFβ family have been reported in the literature to have lower heparin-binding affinity, such as TGF-β3 (See Lyon et al (1997) (26). TGF-β1 has been shown to be heparin-binding at physiological ionic strength, i.e. at 140 mM NaCl. TGF-β3 lacks a key charge and has been demonstrated to be "non-heparin-binding" at physiological conditions. Heparin-affinity chromatography on TGF-β2 by the present inventors demonstrates that it also possesses low-heparin-binding affinity under physiological conditions. The basic domain in each of these growth factors, which could potentially interact with heparin, is underlined in the list of sequences given in Table 2.

Some members of a growth factor family may be heparin-binding, while others are not, as is demonstrated by the TGF-β family. Despite the low-heparin-binding affinity of such "non-heparin-binding" growth factors, they may still be released in a controlled manner from heparin-based delivery systems if they contain a basic domain and the number of heparin-binding sites present in the system is in relatively greater excess to the amount of growth factor to be bound.

EXAMPLE 5

Other "Non-Heparin-Binding" Growth Factors Which Contain Basic Domains

Other families of growth factors also contain growth factors which are not reported in the literature to be heparin-binding, but which contain basic domains(Shown in Table 2.

of at least 0.67. Secondary and tertiary protein structure also influences the heparin-binding affinity of a basic domain within a protein or peptide, and for this reason the formula is approximate. Therefore, it is necessary to perform heparin-affinity chromatography or some other experimental technique to determine the relative heparin affinity of a protein or peptide. The term "low heparin-binding affinity protein" refers only to those proteins or peptides which elute from heparin-affinity chromatography at a NaCl concentration of less than about 140 mM. The formula for sequence analysis described above was applied to the list of growth factors found in Table 2 and used to identify basic domains which could potentially bind to heparin or heparin-like polymers.

Low heparin-binding affinity protein should dissociate rapidly from heparin under physiological conditions. However, surprisingly the results shown in FIG. 3 demonstrate that such low heparin-binding affinity growth factor

TABLE 2

GROWTH FACTOR SEQUENCES

| | | | | | |
|---|---|---|---|---|---|
| TGF-beta1 | ALDTNYCFSS | TEKNCCVRQL | YIDFRKDLGW | KWIHEPKGYH ANFCLGPCPY IWSLDTQYSK VLALYNQHNP | SEQ ID NO:9 |
| TGF-beta2 | ALDAAYCFRN | VQDNCCLRPL | YIDFKRDLGW | KWIHEPKGYN ANFCAGACPY LWSSDTQHSR VLSLYNTINP | SEQ ID NO:10 |
| TGF-beta3 | ALDTNYCFRN | LEENCCVRPL | YIDFRQDLGW | KWVHEPKGYY ANFCSGPCPY LRSADTTHST VLGLYNTLNP | SEQ ID NO:11 |
| TGF-beta1 | GASAAPCCVP | QALEPLPIVY | YVGRKPKVEQ | LSNMIVRSCK CS | SEQ ID NO:12 |
| TGF-beta2 | EASASPCCVS | QDLEPLTILY | YIGKTPKIEQ | LSNMIVKSCK CS | SEQ ID NO:13 |
| TGF-beta3 | EASASPCCVP | QDLEPLTILY | YVGRTPKVEQ | LSNMVVKSCK CS | SEQ ID NO:14 |
| TGF-beta4 | FSQS FREVAGRFLA SEASTHLLVF GMEQRLPPNS ELVQAVLRLF QEPVPQGALH RHGRLSPAAP KARVTVEWLV RDDGSNRTSL IDSRLVSVHE SGWKAFDVTE AVNFWQQLSR PPEPLLVQVS VQREHLGPLA SGAHKLVRFA SQGAPAGLGE PQLELHTLDL RDYGAQGDCD PEAPMTEGTR CCRQEMYIDL QGMKWAKNWV LEPPGFLAYE CVGTCQQPPE ALAFNWPFLG PRQCIASETA SLPMIVSIKE GGRTRPQVVS LPNMRVQKCS CASDGALVPR RLQHRPWCIH | | | | | SEQ ID NO:15 |
| GDNF | SPD KQMAVLPRRE RNRQAAAANP ENSRGKGRRG QRGKNRGCVL TAIHLNVTDL GLGYETKEEL IFRYCSG-SCD | | | | SEQ ID NO:16 |
| Neurturin | LGA RPCGLRELEV RVSELGLGYA SDETVLFRYC AGACEAAARV YDLGLRRLRQ RRRLRRERVR AQPCCRPTAY | | | | SEQ ID NO:17 |
| GDNF | AAETTYDKIL KNLSRNRRLV SDKVGQACCR PIAFDDDLSF LDDNLVYHIL RKHSAKRCGC I | | | | SEQ ID NO:18 |
| Neurturin | EDEVSFLDAH SRYHTVHELS ARECACV | | | | SEQ ID NO:19 |
| NT-4 | GVSETAPASR RGELAVCDAVSG | | | | SEQ ID NO:20 |
| NGF-beta | SSSHPIFHRG | EFSVCDSVSV | WVGDKTTATD | IKGKEVMVLG EVNINNSVFK QYFFETKCRDP NPVDSGCRGID | SEQ ID NO:21 |
| BDNF | HSDPARRGEL | SVCDSISEWV | TAADKKTAVD | MSGGTVTVLE KVPVSKGQLK QYFYETKCNP MGYTKEGCRGID | SEQ ID NO:22 |
| NT-3 | YAEHKSHRGEY | SVCDSESLWV | TDKSSAIDIR | GHQVTVLGE IKTGNSPVK QYFYETRCKE ARPVKNGCRGID | SEQ ID NO:23 |
| NT-4 | WVTDRRTAVD | LRGREVEVLG | EVPAAGGSPL | RQYFFETRCK ADNAEEGGPG AGGGGCRGVD RRHWVSECVD | SEQ ID NO:24 |
| NGF-beta | SKHWNSYCTT | THTFVKALTM | DGKQAAWRF | IRIDTACVCV LSRKAVRRA | SEQ ID NO:25 |
| BDNF | KRHWNSQCRT | TQSYVRALTM | DSKKRIGWRF | IRIDTSCVCT LTIKRGR | SEQ ID NO:26 |
| NT-3 | DKHWNSQCKT | SQTYVRALTS | ENNKLVGWRW | IRIDTSCVCA LSRKIGRT | SEQ ID NO:27 |
| NT-4 | RRHWVSECKA | KQSYVRALTA | DAQGRVGWRW | IRIDTACVCTL LSRTGRA | SEQ ID NO:28 |
| IGF-1A | GP ETLCGAELVD ALQFVCGDRG FYFNKPTGYG SSSRRAPQTG IVDECCFRSC DLRRLEMYCA PLKPAKSA | | | | SEQ ID NO:29 |
| IGF-1B | GP ETLCGAELVD ALQFVCGDRG FYFNKPTGYG SSSRRAPQTG IVDECCFRSC DLRRLEMYCA PLKPAKSA | | | | SEQ ID NO:30 |
| EGF | NSDSECPLSH DGYCLHDGVC MYIEALDKYA CNCVVGYIGE RCQYRDLKWW ELR | | | | SEQ ID NO:31 |

Table 2: Sequences of Low and High heparin-Binding Affinity Growth Factor Proteins.
Basic domains of low heparin-binding affinity growth factor proteins are underlined and basic amino acid residues (K or R) Analysis of the primary protein of growth factors, such as those shown in Table 2 can be used to identity basic domains.

By analyzing the sequences of the TGFβ family and the neurotrophin family, one skilled in the art can observe a pattern in the basic domains underlined in Table 2. From this pattern observed in the basic domains of low heparin-binding affinity proteins, an approximate formula was developed to identify similar basic domains in other proteins. The formula defines a basic domain to be of length about 8 to 30 amino acid residues, comprising at least 2 basic amino acid residues, with a ratio of basic to acidic amino acid residues to at least 2, and a ratio of hydrophobic amino acid residues proteins can be released in a controlled manner from heparin-based delivery systems. This novel result suggests that other growth factors containing domains which meet the requirements of the formula described above may also be released in a controlled manner from heparin-based delivery systems. Examples of such growth factors are shown in the sequence list in Table 2, and the basic domains of these growth factors are underlined.

Two members of the GDNF family, namely neurturin and persephin, both contain basic domains. GDNF is reported in the literature to be heparin-binding, but no reports have been made to date on the heparin-affinity of other members of the GDNF family (27). Neurturin and persephin, based on the analysis presented above, would appear to have sufficient heparin binding affinity to be releasable by the methods and materials of this invention.

IGF-1A and IGF-1B are members of the insulin-like growth factor family. Although there are extensive reports of insulin-like growth factor binding proteins binding to heparin, there is no documentation in the literature of IGF-1A or IGF-1B binding to heparin. Both of these proteins contain basic domains shown in Table 2. Based on the analysis presented above, would appear to have sufficient heparin binding affinity to be releasable by the methods and materials of this invention.

EGF is another growth factor, which contains a basic domain, shown in Table 2, but which is not reported in the literature to be heparin-binding. In fact, the existence of a related growth factor specifically referred to as heparin-binding EGF-like growth factor suggests that EGF does not possess high heparin-affinity. The literature suggests EGF is not heparin-binding based on sequence analysis (45). Based on the analysis presented above, it appears to the present inventors to have sufficient heparin binding affinity to be releasable by the methods and materials of this invention.

Despite the basic domains found in each of these proteins, their heparin-binding affinity is still weak and characterized by elution from heparin-affinity columns at sub-physiological NaCl concentrations (i.e. growth factors which elute between about 25 mM and 140 mM NaCl). For example, heparin-affinity chromatography was performed for NGF-β and TGF-β2. In both cases the proteins were found to elute at 50 mM NaCl at pH 7.4 after several column volumes of buffer, which is well below the physiological NaCl concentration. However, in vitro studies demonstrate that heparin-based release systems can still be used to release NGF-β in a controlled manner, in spite of its relatively low heparin-binding affinity.

All of the growth factors described in the example contain basic domains, but lack any literature reports of heparin-binding affinity. However, based on comparison of the sequences and the results demonstrated with other non-heparin-binding growth factors of the neurotrophin family, sustained release from heparin-based systems should be possible with virtually any growth factor having a basic domain having the characteristics of basic domains described above.

BIBLIOGRAPHY

The following references are specifically incorporated herein by reference for the purposes indicated herein:

1. Presta, M., Satuto, M., Isacchi, A., Caccia, P., Pozzi, A., Gualandris, A., Rusnati, M., Bergonzoni, L., and Sarmientos, P. (1992) *Biochem Biophys Res Commun* 185: 1098–1107
2. Reddi, A. (1998) *Nature Biotechnology* 16: 247–252
3. McCaffrey, T., Falcone, D., and Du, B. (1992) *J Cell Physiol* 152:430–440
4. Spillmann, D., Witt, D., and Lindahl, U. (1998) *J Biol Chem* 273: 15487–15493
5. Götz, R., Köster, R., Winkler, C., Raulf, F., Lottspeich, F., Schartl, M., and Thoenen, H. (1994) *Nature* 372: 266–269
6. Tessler, S., Rockwell, P., Hicklin, D., Cohen, T., Levi, B., Witte, L., Lemischka, I., and Neufeld, G. (1994). *J Biol Chem* 269:12456–12461
7. Kiguchi, K., Beltran, L., Rupp, T., and DiGiovanni, J. (1998) *Mol Carcinog* 22: 73–83
8. Kinosaki, M., Yamagucki, K., Murakarni, A., Ueda, M., Morinaga, T., and Higashio, K. (1998) *Biochim Biophys Acta* 1384: 93–102
9. Steffen, C., Ball-Mirth, D., Harding, P., Bhattacharyya, N., Pillai, S., and Brigstock, D. (1998) *Growth Factors* 15: 199–213
10 Kaneda, N., Talukder, A., Nishiyama, H., Koizumi, S., and Muramatsu, T. (1996) *J Biochem (Tokyo)* 119:1150–1156
11. Nolo, R., Kaksonen, M., and Rauvala, H. (1996). *Eur J Neurosci* 8: 1658–1665
12. Edelman, E., Mathiowitz, E., Langer, R., and Klagsbrun, M. (1991) *Biomaterials* 12: 612–626
13. DeBlois, C., Cote, M.-F., and Doillon, C. (1994) *Biomaterials* 15: 665–672
14. Downs, E., Robertson, N., Riss, T., and Plunkett, M. (1992) *J Cell Physiol* 152: 422–429
15. Houle, J. and Johnson, J. (1989) *Neurosci Lett* 103: 17–23
16. Camarata, P., Suryanarayanan, R., Turner, D., Parker, R., and Ebner, T. (1992) *Neurosurgery* 30: 313–319
17. Powell, E., Sobarzo, M., and Saltzman, W. (1990) *Brain Res* 515: 309–311
18. Maysinger, D., Jalenjak, I., and Cuello, A. (1992) *Neurosci Lett* 140: 71–74
19. Edelman, E., Langer, R., Klagsbum, M., and Mathiowitz, E. (1992) *Controlled Release Systems Containing Heparin and Growth Factors*, MIT: USA
20. Schroeder, J., Bentz, H., and Estridge, T. (1997) *Affinity bound collagen matrices for the delivery of biologically active agents*, Collagen Corporation: USA.
21. Schroeder-Tefft, J., Bentz, H., and Estridge, T. (1997) *J Controlled Release* 49: 291–298
22. Cardin, A. and Weintraub, H. (1989) *Atherosclerosis* 9: 21–32
23. Herbert, C., Bittner, G., and Hubbell, J. (1996) *J Comp Neurol* 365: 380–391
24. Lee, M. and Lander, A. (1991) *Proc Natl Acad Sci USA* 88: 2768–2772
25. Schense, J. and Hubbell, J. (1999) *Bioconjug Chem* 10: 75–81
26. Lyon, M., Rushton, G., and Gallagher, J. (1997) *J Biol Chem* 272: 1800–18006
27. Lin, L.-F. H., Zhang, T., Collins, F., and Arnes, L. (1994) *J Neurochem* 63: 758–768
28. Besson, C, Saulnier J., Wallach, J. (1996) *Analytical Biochemistry* 237: 216–223
29. Coombs G., Bergstrom R., Madison, E., and Corey, D. (1998) *The Journal of Biological Chemisty* 237: 4323–4328
30. Götz, R., Köster, R., Winkler, C., Raulf, F., Lottspeich, F., Shartl, M., and Thoenen, H. (1994) *Nature* 372: 266–269
31. Hata, A., Ridinger, D., Sutherland, S., Emi, M., Shuhua, Z., Myers, R., Ren, K., Cheng, T., Inoue, I., Wilson, D., Iverius, P., and Lalouel, J. (1993) *The Journal of Biological Chemistry* 268: 8847–8457
32. Haugen, P., McCarthy, J., Roche, K., Furcht, L., and Letourneau, P. (1992) *The Journal of Neuroscience* June 2034–2042
33. Kallapur, S. and Akeson, R. (1992) *Journal of Neuroscience Research* 33: 538–548
34. Kaneda, N., Talukder, A., Nishiyama, H., Koizumi, S., and Muramatsu, T. (1996) *J. Biochem* 119: 1150–1156
35. Kiguchi, K., Beltran, L., Rupp, T., and DiGiovanni, J. (1998) *Molecular Carcinogenesis* 22: 73–83
36. Kinosaki, M., Yamaguchi, K., Murakami, A., Ueda, M., Morinaga, T., Higashio, K. (1998) *Biochimica et Biophysica Acta* 1384: 93–102

37. McCaffrey, T., Falcone, D., and Du, B. (1992) *Journal of Cellular Physiology* 152: 430–440
38. Netzel-Arnett, S., Fields, G., Birkedal-Hansen, H., and Van Wart, H. (1991) *The Journal of Biological Chemistry* 266: 6747–6755
39. Nolo, R., Kaksonen, M. and Rauvala, H. (1996) *European Journal of Neuroscience* 8: 1658–1665
40. Smith, M., Shi,L. and Navre, M. (1995) *The Journal of Biological Chemistry* 270: 6440–6449
41. Spillmann, D., Witt, D., and Lindahl, U. (1998) *The Journal of Biological Chemistry* 273: 15487–15493
42. Steffen, C., Ball-Mirth, D., Harding, P., Bhattacharyya, N., Pillai, S., and Brigstock, D. (1998) *Growth Factors* 15: 199–213
43. Presta, et al. (1992) *Biochemical and Biophysical Research Communications,* 185: 1098–1107 (1992)
44. Zucker, M. and Katz, I., (1991) *Society for Experimental Biology and Medicine:* 693–702
45. Higashiyama S., Abraham J. A., Miller J., Fiddes, J. C., and Klagsbrun, M. (1991) *Science* 251 (4996): 936–9
46. Maaroufi, R. M., Jozefowicz, M., Tapon-Bretaudiere J., Jozefonwicz, J., Fischer, A. M., Biomaterials 1997, 18:359–366.
47. Logeart, D., Prrgent-Richard, S., Jozefonwicz, J., Letourneur, D., Eur J Cell Biol 1997, 74:376–384.
48. de Raucourt, E., Maurat, S., Chaubet, F., Maiga-Revel, O., Jozefonwicz, M., Fischer, A. M., J. Biomed Mater Res 1998, 41 :49–57
49. Bagheri-Yamand, R., Kourbali, Y., Mabilat, C., Morere, J. F., Martin, A., Lu, H., Soria, C., Jozefonwicz, J., Crepin, M., Br. J. Cancer 1998, 78:111–118.
50. Silver, J. H., Hart, A. P., Williams, E. C., Cooper S. L., Charef, S., Labarre, D., Jozefowicz, M., Biomaterials 1992, 13:339–344.
51. U.S. Pat. No. 5,830,700 Irani, Meher

What is claimed is:

1. A drug delivery composition comprising:
   a) a substrate;
   b) a bi-domain peptide comprising a first domain that binds heparin or heparin-like compounds with high affinity and a second domain that binds to the substrate, wherein the second domain is covalently bound to the substrate so that the first domain is able to bind to heparin or heparin-like compounds;
   c) heparin or a heparin-like polymer;
   d) a protein growth factor or a peptide fragment thereof having a domain that binds heparin with low affinity, wherein the protein growth factor or a peptide fragment thereof binds with low affinity to the heparin or heparin-like polymer of (c), and wherein low affinity is defined as not binding with the heparin or heparin-like polymer of(c) at a NaCl concentration of between about 25 mM and 140 mM.

2. The composition of claim 1 wherein the domain of the growth factor or peptide fragment thereof is further defined as comprising a length of about 8 to 30 amino acid residues comprising at least 2 basic amino acid residues, a ratio of basic to acidic amino acid residues of at least 2, and a ratio of hydrophobic amino acid residues to basic amino acid residues of at least 0.67.

3. The composition of claim 2 wherein the basic amino acid residues are K or R.

4. The composition of claim 2 wherein the acidic amino acid residues are further defined as D or E.

5. The composition of claim 2 wherein the hydrophobic amino acid residues are further defined as A, V, F, P, M, I, or L or C when C is involved in a disulfide bond.

6. The composition of claim 2 wherein the growth factor or peptide fragment thereof is selected from the group consisting of neurturin persephin, IGF-1A, IGF-1β, EGF, NGFβ, NT-3, BDNF, NT-4, TGF-β3, and TOF-β4.

7. The composition of claim 1 wherein the molar ratio of heparin or heparin-like polymer to growth factor or peptide fragment thereof is at least one.

8. The composition of claim 1 in a vascular graft.

9. The composition of claim 1 in an article for treatment of dermal wounds.

10. The composition of claim 9, wherein the growth factor is TGF-β3.

11. The composition of claim 1 in an implantable sterilized composition.

12. The composition of claim 1, wherein the heparin or heparin-like compound is non-covalently attached to the peptide.

13. The composition of claim 1 wherein the substrate is selected from the group comprising fibrin, collagen and synthetic polymer hydrogels.

14. The composition of claim 13 wherein the comprises fibrin.

15. The composition of claim 13 wherein the substrate comprises a synthetic polymer hydrogel.

16. The composition of claim 12 wherein the heparin or heparin-like polymer has a molecular weight between about 3,000 and 10,000,000 Daltons.

17. The composition of claim 12 wherein the heparin-like polymer is a polysaccharide having a molecular weight between about 3,000 and 10,000,000 Daltons, and having at least one negative charge per two saccharide rings and no more than one positive charge per ten saccharide rings.

18. The composition of claim 1, wherein the heparin-like polymer is selected from the group consisting of dextran sulfates, chondroitin sulfates, heparin sulfates, fucans, and alginates.

19. A method for providing controlled release of a growth factor comprising:
   preparing a composition comprising:
      a) a substrate;
      b) a bi-domain peptide comprising a first domain that binds heparin or heparin-like compounds with high affinity and a second domain that binds to the substrate, wherein the second domain is covalently bound to the substrate so that the first domain is able to bind to heparin or heparin-like compounds;
      c) heparin or a heparin-like polymer;
      d) a protein growth factor or a peptide fragment thereof having a domain that binds heparin with low affinity, wherein the protein growth factor or a peptide fragment thereof binds with low affinity to the heparin or heparin-like polymer of(c), and wherein low affinity is defined as not binding with the heparin or heparin-like polymer of(c) at a NaCl concentration of between about 25 mM and 140 mM, and placing the composition on a wound in need thereof.

20. The method of claim 19, wherein the growth factor or a peptide fragment thereof is released by dissociation of the growth factor from the heparin or heparin-like polymer.

* * * * *

SEQUENCE LISTING

```
<160> NUMBER OF SEQ ID NOS: 31

<210> SEQ ID NO 1
<211> LENGTH: 14
<212> TYPE: PRT
<213> ORGANISM: Homo sapiens
<220> FEATURE:
<221> NAME/KEY: MOD_RES
<222> LOCATION: (2)
<223> OTHER INFORMATION: Xaa is bAla (Beta Alanine)

<400> SEQUENCE: 1

Lys Xaa Phe Ala Lys Leu Ala Ala Arg Leu Tyr Arg Lys Ala
 1               5                  10

<210> SEQ ID NO 2
<211> LENGTH: 8
<212> TYPE: PRT
<213> ORGANISM: Homo sapiens

<400> SEQUENCE: 2

Tyr Lys Lys Ile Ile Lys Lys Leu
 1               5

<210> SEQ ID NO 3
<211> LENGTH: 14
<212> TYPE: PRT
<213> ORGANISM: Homo sapiens

<400> SEQUENCE: 3

Lys His Lys Gly Arg Asp Val Ile Leu Lys Lys Asp Val Arg
 1               5                  10

<210> SEQ ID NO 4
<211> LENGTH: 14
<212> TYPE: PRT
<213> ORGANISM: Homo sapiens
<220> FEATURE:
<221> NAME/KEY: MOD_RES
<222> LOCATION: (2)
<223> OTHER INFORMATION: Xaa is bALA (Beta Alanine)

<400> SEQUENCE: 4

Arg Xaa Phe Ala Arg Leu Ala Ala Arg Leu Tyr Arg Arg Ala
 1               5                  10
```

<210> SEQ ID NO 5
<211> LENGTH: 12
<212> TYPE: PRT
<213> ORGANISM: Homo sapiens

<400> SEQUENCE: 5

Lys Asp Pro Lys Arg Leu Tyr Arg Ser Arg Lys Tyr
 1               5                  10

<210> SEQ ID NO 6
<211> LENGTH: 11
<212> TYPE: PRT
<213> ORGANISM: Homo sapiens

<400> SEQUENCE: 6

Cys Val Leu Ser Arg Lys Ala Val Arg Ala
 1               5                  10

<210> SEQ ID NO 7
<211> LENGTH: 10
<212> TYPE: PRT
<213> ORGANISM: Homo sapiens

<400> SEQUENCE: 7

Cys Ala Leu Ser Arg Lys Ile Gly Arg Thr
 1               5                  10

<210> SEQ ID NO 8
<211> LENGTH: 9
<212> TYPE: PRT
<213> ORGANISM: Homo sapiens

<400> SEQUENCE: 8

Cys Thr Leu Thr Ile Lys Arg Gly Arg
 1               5

<210> SEQ ID NO 9
<211> LENGTH: 70
<212> TYPE: PRT
<213> ORGANISM: Homo sapiens

<400> SEQUENCE: 9

Ala Leu Asp Thr Asn Tyr Cys Phe Ser Thr Glu Lys Asn Cys Cys
 1               5                  10                  15

Val Arg Gln Leu Tyr Ile Asp Phe Arg Lys Asp Leu Gly Trp Lys Trp
                20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
        50                  55                  60

Tyr Asn Gln His Asn Pro
65                  70

<210> SEQ ID NO 10
<211> LENGTH: 70
<212> TYPE: PRT
<213> ORGANISM: Homo sapiens

<400> SEQUENCE: 10

Ala Leu Asp Ala Ala Tyr Cys Phe Arg Asn Val Gln Asp Asn Cys Cys
 1               5                  10                  15

```
Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro
65              70

<210> SEQ ID NO 11
<211> LENGTH: 70
<212> TYPE: PRT
<213> ORGANISM: Homo sapiens

<400> SEQUENCE: 11

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro
65              70

<210> SEQ ID NO 12
<211> LENGTH: 42
<212> TYPE: PRT
<213> ORGANISM: Homo sapiens

<400> SEQUENCE: 12

Gly Ala Ser Ala Ala Pro Cys Cys Val Pro Gln Ala Leu Glu Pro Leu
1               5                   10                  15

Pro Ile Val Tyr Tyr Val Gly Arg Lys Pro Lys Val Glu Gln Leu Ser
            20                  25                  30

Asn Met Ile Val Arg Ser Cys Lys Cys Ser
        35                  40

<210> SEQ ID NO 13
<211> LENGTH: 42
<212> TYPE: PRT
<213> ORGANISM: Homo sapiens

<400> SEQUENCE: 13

Glu Ala Ser Ala Ser Pro Cys Cys Val Ser Gln Asp Leu Glu Pro Leu
1               5                   10                  15

Thr Ile Leu Tyr Tyr Ile Gly Lys Thr Pro Lys Ile Glu Gln Leu Ser
            20                  25                  30

Asn Met Ile Val Lys Ser Cys Lys Cys Ser
        35                  40

<210> SEQ ID NO 14
<211> LENGTH: 42
<212> TYPE: PRT
<213> ORGANISM: Homo sapiens

<400> SEQUENCE: 14

Glu Ala Ser Ala Ser Pro Cys Cys Val Pro Gln Asp Leu Glu Pro Leu
1               5                   10                  15
```

```
Thr Ile Leu Tyr Tyr Val Gly Arg Thr Pro Lys Val Glu Gln Leu Ser
            20                  25                  30

Asn Met Val Val Lys Ser Cys Lys Cys Ser
        35                  40

<210> SEQ ID NO 15
<211> LENGTH: 294
<212> TYPE: PRT
<213> ORGANISM: Homo sapiens

<400> SEQUENCE: 15

Phe Ser Gln Ser Phe Arg Glu Val Ala Gly Arg Phe Leu Ala Ser Glu
  1               5                  10                  15

Ala Ser Thr His Leu Leu Val Phe Gly Met Glu Gln Arg Leu Pro Pro
            20                  25                  30

Asn Ser Glu Leu Val Gln Ala Val Leu Arg Leu Phe Gln Glu Pro Val
        35                  40                  45

Pro Gln Gly Ala Leu His Arg His Gly Arg Leu Ser Pro Ala Ala Pro
    50                  55                  60

Lys Ala Arg Val Thr Val Glu Trp Leu Val Arg Asp Asp Gly Ser Asn
 65                  70                  75                  80

Arg Thr Ser Leu Ile Asp Ser Arg Leu Val Ser Val His Glu Ser Gly
                85                  90                  95

Trp Lys Ala Phe Asp Val Thr Glu Ala Val Asn Phe Trp Gln Gln Leu
            100                 105                 110

Ser Arg Pro Pro Glu Pro Leu Leu Val Gln Val Ser Val Gln Arg Glu
        115                 120                 125

His Leu Gly Pro Leu Ala Ser Gly Ala His Lys Leu Val Arg Phe Ala
    130                 135                 140

Ser Gln Gly Ala Pro Ala Gly Leu Gly Glu Pro Gln Leu Glu Leu His
145                 150                 155                 160

Thr Leu Asp Leu Arg Asp Tyr Gly Ala Gln Gly Asp Cys Asp Pro Glu
                165                 170                 175

Ala Pro Met Thr Glu Gly Thr Arg Cys Cys Arg Gln Glu Met Tyr Ile
            180                 185                 190

Asp Leu Gln Gly Met Lys Trp Ala Lys Asn Trp Val Leu Glu Pro Pro
        195                 200                 205

Gly Phe Leu Ala Tyr Glu Cys Val Gly Thr Cys Gln Gln Pro Pro Glu
    210                 215                 220

Ala Leu Ala Phe Asn Trp Pro Phe Leu Gly Pro Arg Gln Cys Ile Ala
225                 230                 235                 240

Ser Glu Thr Ala Ser Leu Pro Met Ile Val Ser Ile Lys Glu Gly Gly
                245                 250                 255

Arg Thr Arg Pro Gln Val Val Ser Leu Pro Asn Met Arg Val Gln Lys
            260                 265                 270

Cys Ser Cys Ala Ser Asp Gly Ala Leu Val Pro Arg Arg Leu Gln His
        275                 280                 285

Arg Pro Trp Cys Ile His
    290

<210> SEQ ID NO 16
<211> LENGTH: 73
<212> TYPE: PRT
<213> ORGANISM: Homo sapiens

<400> SEQUENCE: 16
```

Ser Pro Asp Lys Gln Met Ala Val Leu Pro Arg Arg Glu Arg Asn Arg
1               5                   10                  15

Gln Ala Ala Ala Asn Pro Glu Asn Ser Arg Gly Lys Gly Arg Arg
            20                  25                  30

Gly Gln Arg Gly Lys Asn Arg Gly Cys Val Leu Thr Ala Ile His Leu
        35                  40                  45

Asn Val Thr Asp Leu Gly Leu Gly Tyr Glu Thr Lys Glu Glu Leu Ile
    50                  55                  60

Phe Arg Tyr Cys Ser Gly Ser Cys Asp
65                  70

<210> SEQ ID NO 17
<211> LENGTH: 73
<212> TYPE: PRT
<213> ORGANISM: Homo sapiens

<400> SEQUENCE: 17

Leu Gly Ala Arg Pro Cys Gly Leu Arg Glu Leu Glu Val Arg Val Ser
1               5                   10                  15

Glu Leu Gly Leu Gly Tyr Ala Ser Asp Glu Thr Val Leu Phe Arg Tyr
            20                  25                  30

Cys Ala Gly Ala Cys Glu Ala Ala Arg Val Tyr Asp Leu Gly Leu
        35                  40                  45

Arg Arg Leu Arg Gln Arg Arg Arg Leu Arg Arg Glu Arg Val Arg Ala
    50                  55                  60

Gln Pro Cys Cys Arg Pro Thr Ala Tyr
65                  70

<210> SEQ ID NO 18
<211> LENGTH: 61
<212> TYPE: PRT
<213> ORGANISM: Homo sapiens

<400> SEQUENCE: 18

Ala Ala Glu Thr Thr Tyr Asp Lys Ile Leu Lys Asn Leu Ser Arg Asn
1               5                   10                  15

Arg Arg Leu Val Ser Asp Lys Val Gly Gln Ala Cys Cys Arg Pro Ile
            20                  25                  30

Ala Phe Asp Asp Asp Leu Ser Phe Leu Asp Asp Asn Leu Val Tyr His
        35                  40                  45

Ile Leu Arg Lys His Ser Ala Lys Arg Cys Gly Cys Ile
    50                  55                  60

<210> SEQ ID NO 19
<211> LENGTH: 27
<212> TYPE: PRT
<213> ORGANISM: Homo sapiens

<400> SEQUENCE: 19

Glu Asp Glu Val Ser Phe Leu Asp Ala His Ser Arg Tyr His Thr Val
1               5                   10                  15

His Glu Leu Ser Ala Arg Glu Cys Ala Cys Val
            20                  25

<210> SEQ ID NO 20
<211> LENGTH: 22
<212> TYPE: PRT
<213> ORGANISM: Homo sapiens

```
<400> SEQUENCE: 20

Gly Val Ser Glu Thr Ala Pro Ala Ser Arg Arg Gly Glu Leu Ala Val
 1               5                  10                  15

Cys Asp Ala Val Ser Gly
             20

<210> SEQ ID NO 21
<211> LENGTH: 72
<212> TYPE: PRT
<213> ORGANISM: Homo sapiens

<400> SEQUENCE: 21

Ser Ser Ser His Pro Ile Phe His Arg Gly Glu Phe Ser Val Cys Asp
 1               5                  10                  15

Ser Val Ser Val Trp Val Gly Asp Lys Thr Thr Ala Thr Asp Ile Lys
             20                  25                  30

Gly Lys Glu Val Met Val Leu Gly Glu Val Asn Ile Asn Asn Ser Val
         35                  40                  45

Phe Lys Gln Tyr Phe Phe Glu Thr Lys Cys Arg Asp Pro Asn Pro Val
     50                  55                  60

Asp Ser Gly Cys Arg Gly Ile Asp
 65                  70

<210> SEQ ID NO 22
<211> LENGTH: 72
<212> TYPE: PRT
<213> ORGANISM: Homo sapiens

<400> SEQUENCE: 22

His Ser Asp Pro Ala Arg Arg Gly Glu Leu Ser Val Cys Asp Ser Ile
 1               5                  10                  15

Ser Glu Trp Val Thr Ala Ala Asp Lys Lys Thr Ala Val Asp Met Ser
             20                  25                  30

Gly Gly Thr Val Thr Val Leu Glu Lys Val Pro Val Ser Lys Gly Gln
         35                  40                  45

Leu Lys Gln Tyr Phe Tyr Glu Thr Lys Cys Asn Pro Met Gly Tyr Thr
     50                  55                  60

Lys Glu Gly Cys Arg Gly Ile Asp
 65                  70

<210> SEQ ID NO 23
<211> LENGTH: 71
<212> TYPE: PRT
<213> ORGANISM: Homo sapiens

<400> SEQUENCE: 23

Tyr Ala Glu His Lys Ser His Arg Gly Glu Tyr Ser Val Cys Asp Ser
 1               5                  10                  15

Glu Ser Leu Trp Val Thr Asp Lys Ser Ser Ala Ile Asp Ile Arg Gly
             20                  25                  30

His Gln Val Thr Val Leu Gly Glu Ile Lys Thr Gly Asn Ser Pro Val
         35                  40                  45

Lys Gln Tyr Phe Tyr Glu Thr Arg Cys Lys Glu Ala Arg Pro Val Lys
     50                  55                  60

Asn Gly Cys Arg Gly Ile Asp
 65                  70

<210> SEQ ID NO 24
```

```
<211> LENGTH: 70
<212> TYPE: PRT
<213> ORGANISM: Homo sapiens

<400> SEQUENCE: 24

Trp Val Thr Asp Arg Arg Thr Ala Val Asp Leu Arg Gly Arg Glu Val
  1               5                  10                  15

Glu Val Leu Gly Glu Val Pro Ala Ala Gly Gly Ser Pro Leu Arg Gln
             20                  25                  30

Tyr Phe Phe Glu Thr Arg Cys Lys Ala Asp Asn Ala Glu Glu Gly Gly
         35                  40                  45

Pro Gly Ala Gly Gly Gly Cys Arg Gly Val Asp Arg Arg His Trp
     50                  55                  60

Val Ser Glu Cys Val Asp
 65                  70

<210> SEQ ID NO 25
<211> LENGTH: 48
<212> TYPE: PRT
<213> ORGANISM: Homo sapiens

<400> SEQUENCE: 25

Ser Lys His Trp Asn Ser Tyr Cys Thr Thr Thr His Thr Phe Val Lys
  1               5                  10                  15

Ala Leu Thr Met Asp Gly Lys Gln Ala Ala Trp Arg Phe Ile Arg Ile
             20                  25                  30

Asp Thr Ala Cys Val Cys Val Leu Ser Arg Lys Ala Val Arg Arg Ala
         35                  40                  45

SEQ ID NO 26
LENGTH: 47
<212> TYPE: PRT
<213> ORGANISM: Homo sapiens

<400> SEQUENCE: 26

Lys Arg His Trp Asn Ser Gln Cys Arg Thr Thr Gln Ser Tyr Val Arg
  1               5                  10                  15

Ala Leu Thr Met Asp Ser Lys Lys Arg Ile Gly Trp Arg Phe Ile Arg
             20                  25                  30

Ile Asp Thr Ser Cys Val Cys Thr Leu Thr Ile Lys Arg Gly Arg
         35                  40                  45

<210> SEQ ID NO 27
<211> LENGTH: 48
<212> TYPE: PRT
<213> ORGANISM: Homo sapiens

<400> SEQUENCE: 27

Asp Lys His Trp Asn Ser Gln Cys Lys Thr Ser Gln Thr Tyr Val Arg
  1               5                  10                  15

Ala Leu Thr Ser Glu Asn Asn Lys Leu Val Gly Trp Arg Trp Ile Arg
             20                  25                  30

Ile Asp Thr Ser Cys Val Cys Ala Leu Ser Arg Lys Ile Gly Arg Thr
         35                  40                  45

<210> SEQ ID NO 28
<211> LENGTH: 48
<212> TYPE: PRT
<213> ORGANISM: Homo sapiens

<400> SEQUENCE: 28
```

```
Arg Arg His Trp Val Ser Glu Cys Lys Ala Lys Gln Ser Tyr Val Arg
 1               5                  10                  15

Ala Leu Thr Ala Asp Ala Gln Gly Arg Val Gly Trp Arg Trp Ile Arg
             20                  25                  30

Ile Asp Thr Ala Cys Val Cys Thr Leu Leu Ser Arg Thr Gly Arg Ala
             35                  40                  45
```

<210> SEQ ID NO 29
<211> LENGTH: 70
<212> TYPE: PRT
<213> ORGANISM: Homo sapiens

<400> SEQUENCE: 29

```
Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
             20                  25                  30

Ser Ser Ser Arg Arg Ala Pro Gln Thr Gly Ile Val Asp Glu Cys Cys
             35                  40                  45

Phe Arg Ser Cys Asp Leu Arg Arg Leu Glu Met Tyr Cys Ala Pro Leu
     50                  55                  60

Lys Pro Ala Lys Ser Ala
 65                  70
```

<210> SEQ ID NO 30
<211> LENGTH: 70
<212> TYPE: PRT
<213> ORGANISM: Homo sapiens

<400> SEQUENCE: 30

```
Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
             20                  25                  30

Ser Ser Ser Arg Arg Ala Pro Gln Thr Gly Ile Val Asp Glu Cys Cys
             35                  40                  45

Phe Arg Ser Cys Asp Leu Arg Arg Leu Glu Met Tyr Cys Ala Pro Leu
     50                  55                  60

Lys Pro Ala Lys Ser Ala
 65                  70
```

<210> SEQ ID NO 31
<211> LENGTH: 53
<212> TYPE: PRT
<213> ORGANISM: Homo sapiens

<400> SEQUENCE: 31

```
Asn Ser Asp Ser Glu Cys Pro Leu Ser His Asp Gly Tyr Cys Leu His
 1               5                  10                  15

Asp Gly Val Cys Met Tyr Ile Glu Ala Leu Asp Lys Tyr Ala Cys Asn
             20                  25                  30

Cys Val Val Gly Tyr Ile Gly Glu Arg Cys Gln Tyr Arg Asp Leu Lys
             35                  40                  45

Trp Trp Glu Leu Arg
     50
```